(12) United States Patent
Hofstadter et al.

(10) Patent No.: US 8,060,200 B2
(45) Date of Patent: *Nov. 15, 2011

(54) SELF-ADJUSTING OPTIMAL WAVEFORMS

(75) Inventors: Steve Hofstadter, Los Angeles, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 12/131,736

(22) Filed: Jun. 2, 2008

(65) Prior Publication Data
US 2008/0249582 A1  Oct. 9, 2008

Related U.S. Application Data

(63) Continuation of application No. 11/102,331, filed on Apr. 7, 2005, now Pat. No. 7,398,122.

(51) Int. Cl.
*A61N 1/39* (2006.01)
(52) U.S. Cl. ............... 607/8; 607/5; 607/14; 607/15
(58) Field of Classification Search .............. 607/4, 5, 607/14, 15
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,230,336 A | 7/1993 | Fain et al. | |
| 5,391,186 A | 2/1995 | Kroll et al. | |
| 5,466,254 A | 11/1995 | Helland | |
| 5,476,483 A | 12/1995 | Bornzin et al. | |
| 5,522,854 A * | 6/1996 | Ideker et al. | 607/6 |
| 5,531,764 A | 7/1996 | Adams et al. | |
| 5,540,723 A | 7/1996 | Ideker et al. | |
| 5,991,658 A | 11/1999 | Brewer et al. | |
| 6,141,585 A * | 10/2000 | Prutchi et al. | 607/8 |
| 6,198,967 B1 | 3/2001 | Brewer et al. | |
| 6,314,323 B1 | 11/2001 | Ekwall | |
| 6,643,545 B2 | 11/2003 | Ideker et al. | |
| 6,647,290 B2 | 11/2003 | Wuthrich | |
| 2001/0053925 A1 | 12/2001 | Ideker et al. | |

FOREIGN PATENT DOCUMENTS

| | | |
|---|---|---|
| EP | 0722349 B1 | 12/1999 |
| EP | 0782870 B1 | 6/2003 |
| WO | 9509673 | 4/1995 |
| WO | 9516492 | 6/1995 |

OTHER PUBLICATIONS

Bardy, Gust H. MD et al., "Truncated Biphasic Pulses for Transthoracic Defibrillation," Circulation. 1995;91:1768-1774.

(Continued)

*Primary Examiner* — Scott Getzow
*Assistant Examiner* — Joseph Dietrich

(57) ABSTRACT

An exemplary method includes detecting fibrillation, measuring impedance of a defibrillation circuit that includes myocardial tissue, determining one or more defibrillation shock parameters based at least in part on the impedance, delivering a defibrillation shock using the one or more defibrillation shock parameters and, if the shock was unsuccessful, adjusting a membrane time constant and determining one or more new defibrillation shock parameters based at least in part on the adjusted membrane time constant. Various other exemplary methods are disclosed as well as various exemplary devices, systems, etc.

16 Claims, 13 Drawing Sheets

OTHER PUBLICATIONS

Cheng, Yuanna et al., "Mechanisms of shock-induced arrhythmogenesis during acute global ischemia," Am J Physiol Heart Circ Physiol. 2002;282:H2141-H2151.

Gold, Michael R. PhD et al., "Strength-Duration Relationship for Human Transvenous Defibrillation," Circulation. 1997;96:3517-3520.

Irnich, Werner, "How to Program Pulse Duration or Tilt in Implantable Cardioverter Defibrillators," Pace. 2003;26(Pt. II):453-456.

Mowrey, K.A et al., "Kinetics of defibrillation shock-induced response: design implications for the optimal defibrillation waveform," Europace. 2002;4:27-39.

Mowrey, Kent A. et al., "Kinetics of Shock-Induced Transmembrane Polarization: Effect of Ischemia," JAAC—Cardiac Arrhythmias. Mar. 2002—Abstract.

Qu, Fujian et al., "The Gurvich waveform has lower defibrillation threshold than the rectilinear waveform and the truncated exponential waveform in the rabbit heart," Can J Physiol Pharmacol. 2005;83:152-160.

Swerdlow, Charles D. MD et al., "Application of Models of Defibrillation to Human Defibrillation Data—Implications for Optimizing Implantable Defibrillator Capacitance," Circulation. 1997;96:2813-2822.

NonFinal Office Action, mailed Nov. 26, 2007: Parent U.S. Appl. No. 11/102,331.

Notice of Allowance, mailed May 26, 2008: Parent U.S. Appl. No. 11/102,331.

NonFinal Office Action, mailed Mar. 27, 2007: Related U.S. Appl. No. 11/102,331.

Notice of Allowance, mailed Jun. 8, 2007: Related U.S. Appl. No. 11/102,331.

* cited by examiner

Exemplary Method
800

SELF-ADJUSTING OPTIMAL WAVEFORMS

CROSS-REFERENCE TO RELATED APPLICATIONS

This application is a continuation of U.S. patent application Ser. No. 11/102,331, filed Apr. 7, 2005, titled "Self Adjusting Optimal Waveforms," now U.S. Pat. No. 7,398,122; and is related to U.S. patent application Ser. No. 11/102,002, filed Apr. 7, 2005, titled "Self Adjusting Optimal Waveforms," now U.S. Pat. No. 7,283,871.

TECHNICAL FIELD

Subject matter presented herein generally relates to implantable defibrillation devices. Various exemplary methods, devices, systems, etc., concern selection or determination of one or more defibrillation shock parameters.

BACKGROUND

Implantable cardiac defibrillators (ICDs) perform two main functions: detecting fibrillation and delivering defibrillation shocks. A variety of issues are associated with use of ICDs. Some issues pertain to the patient while others pertain to the ICD. For example, an ICD should extend patient life and even improve quality of life. On the other hand, an ICD should operate efficiently to conserve its limited power supply.

Efficient operation of an ICD involves delivering defibrillation shocks only when required, delivering an initial defibrillation shock that has a high likelihood of success, and delivering defibrillation shocks at energy levels that are not greatly in excess of a minimum required energy level. The first factor depends largely on fibrillation detection algorithms and ICD capabilities related thereto while the second and third operational factors are interrelated.

Many studies have tried to divine "optimal" shock parameters. For example, a study by Inrich "How to program pulse duration or tilt in implantable cardioverter defibrillators," Pacing Clin Electrophysiol. 2003 January; 26(1 Pt 2): 453-6, presented a system of three related equations in an effort to determine optimal defibrillation shock parameters. While such studies are instructive, a need still exists for better methods to determine or optimize defibrillation shock parameters. Yet further, as described herein, judicious selection of parameters or models or analysis of defibrillation shock information can even yield insight as to cardiac condition.

SUMMARY

An exemplary method includes detecting fibrillation, measuring impedance of a defibrillation circuit that includes myocardial tissue, determining one or more defibrillation shock parameters based at least in part on the impedance, delivering a defibrillation shock using the one or more defibrillation shock parameters and, if the shock was unsuccessful, adjusting a membrane time constant and determining one or more new defibrillation shock parameters based at least in part on the adjusted membrane time constant. Various other exemplary methods are disclosed as well as various exemplary devices, systems, etc.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are optionally implemented in connection with any stimulation device that is configured or configurable to stimulate and/or shock tissue.

Figure 1:
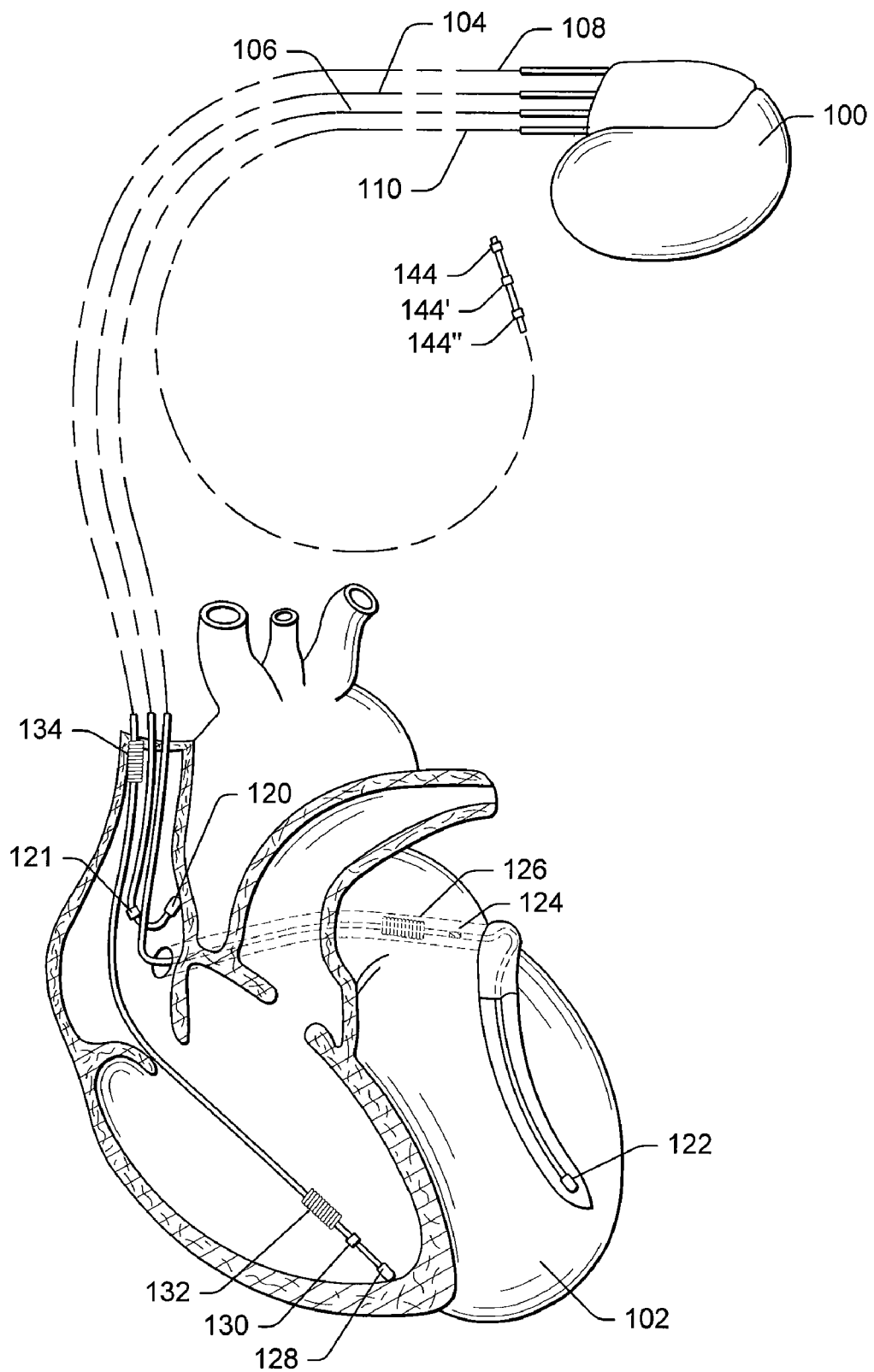
FIG. 1 is a simplified diagram illustrating an exemplary implantable stimulation device in electrical communication with at least three leads implanted into a patient's heart and at least one other lead for delivering stimulation and/or shock therapy. Other examples may include a different number of leads (e.g., fewer or more).

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
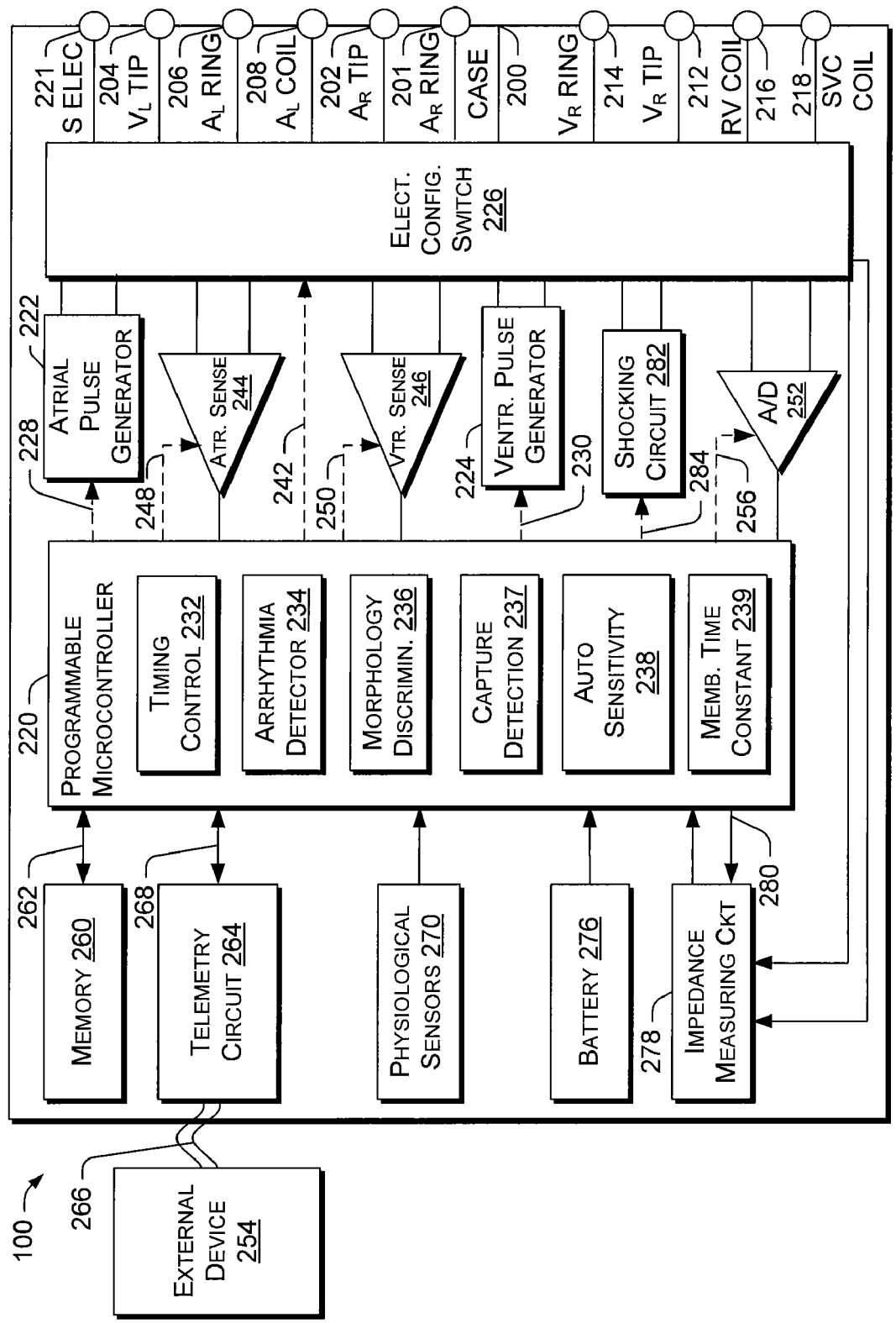
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING)

214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, an auto sensitivity module 238, a membrane time constant module module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The membrane time constant module 239 may perform a variety of tasks related to, for example, selection, determination, estimation, etc., of a membrane time constant. Further, the module 239 may aid in ischemia determinations or decisions. For example, as described herein, a membrane time constant may indicate whether a patient has ischemia. The module 239 optionally relies on a variety of information, for example, the module 239 may rely on impedance measurements of a defibrillation shock circuit that includes tissue, fluid, etc., (generally myocardial tissue). The module 239 may aid in determining one or more defibrillation shock parameters (e.g., energy, leading edge voltage, duration, phase, waveform type, timing, electrode configuration, etc.). In general, determining a parameter means determining a value, whether the value is an energy, a voltage, a duration, a number of phases, etc. For example, determining a leading edge voltage parameter means determining a leading edge voltage suitable for use in delivery of a shock. The module 239 may operate prior to delivery of a shock or during delivery of a shock or during a shock delivery period (e.g., shock duration).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. As already mentioned, the circuit 278 may provide impedance information to the membrane time constant module 239. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two or more current pathways.

Figure 3:
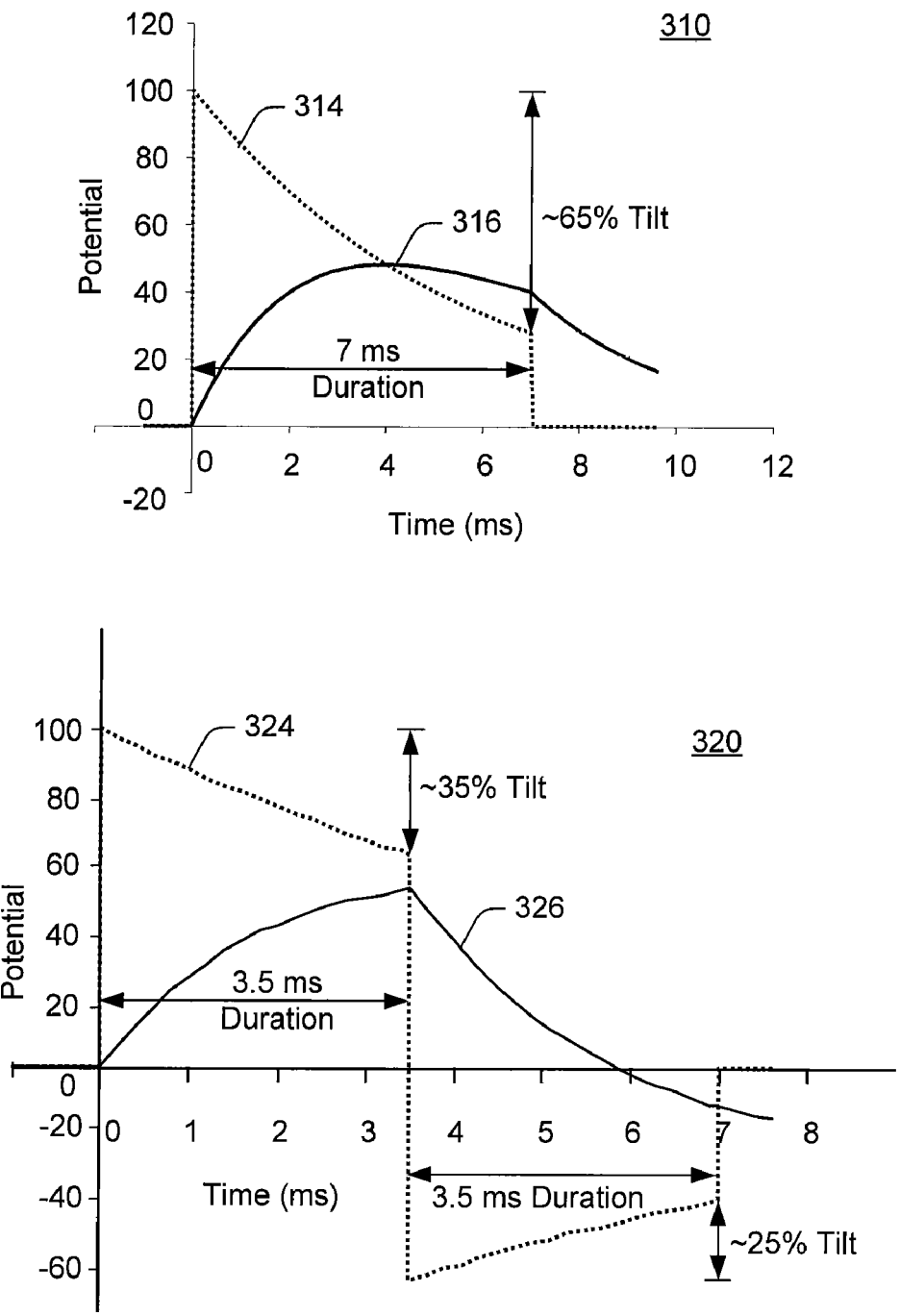
FIG. 3 is a plot of potential versus time for a monophasic defibrillation shock and membrane response thereto and a plot of potential versus time for a biphasic defibrillation shock and membrane response thereto.

FIG. 3 shows a plot of potential versus time 310 for a defibrillation shock. More specifically, the plot 310 shows a monophasic, truncated exponential waveform 314 and a corresponding myocardial or membrane response 316. The waveform or "pulse" 314 may be characterized in part by a parameter called "tilt" and a duration parameter. Tilt is defined as the leading edge voltage at or near an initial time, which is typically the maximum voltage, minus the voltage at the end of the duration divided by the leading edge voltage. Thus, for the example in the plot 310, the waveform has a tilt of approximately 65% while the duration of the shock waveform is about 7 ms. Monophasic, truncated exponential waveforms may be characterized by leading edge voltage, tilt and duration. The leading edge voltage typically depends on resistance or impedance of the tissue into which the shock is delivered and the capacitor(s) used to store charge. Many have described this relationship using an RC circuit, noting that a given tilt and RC circuit parameters may determine the duration, that a given duration and RC parameters may determine tilt, etc.

During delivery of the shock, the membrane is charged and its potential increases. Various optical and electrode mapping studies have revealed the shape of the membrane, which may be characterized by a membrane time constant ($\tau$) according to the following equation:

$$V(t)/V_{max} = (1 - e^{-t/\tau}) \tag{1}$$

where V(t) is the potential with respect to time t and $V_{max}$ is the maximum potential prior to activation. Such studies indicate that, in humans, the time constant in healthy adults is about 3.5 ms (note that the time constant in the plot is considerably shorter). Models other than that of Eqn. 1 may be used for membrane time constant.

A study by Gold et al., "Strength-Duration Relationship for Human Transvenous Defibrillation," Circulation. 1997; 96: 3517-3520, noted that the strength-duration relationship for human transvenous defibrillation is unaffected by pulse widths greater than 6 ms and that these data were consistent with a parallel circuit model (which differs from Eqn. 1) having a membrane time constant of 5.3 ms. Gold et al. further state that delivered energy is minimized at 5 to 6 ms, "indicating that this is the most efficient pulse widths for monophasic defibrillation and should serve as the basis for the first phase of biphasic waveforms."

In the plot 310, the data correspond to a capacitor charged to 100% of its voltage and then discharged to deliver the monophasic shock. The cell membrane potential increases during delivery of the shock and reaches a peak at about 4 ms. However, the shock duration (i.e., duration of the monophasic waveform) is greater than the time required by the membrane to reach the peak. Thus, energy is wasted and the membrane subjected to more energy than necessary to achieve the peak potential. Further, the extended duration of the shock is counterproductive as it reduces the final membrane response.

FIG. 3 also shows a plot of potential versus time 320 for another defibrillation shock. More specifically, the plot 320 shows a biphasic, truncated exponential waveform 324 and a corresponding myocardial or membrane response 326. Biphasic, truncated exponential waveforms may be characterized in part by a duration of a first phase and a duration of a second phase. In general, an overall tilt (T) may be given, for example, the waveform 324 has an overall tilt of about 50% (T=1−$V_{trailing}/V_{leading}$).

During delivery of the shock, the membrane is charged and its potential increases. However, in contrast to the monophasic shock, the second phase of the biphasic shock commences at about the peak (e.g., approximately 3.5 ms) and acts to decrease the membrane potential.

If during the first phase, the cell is captured, a new activation potential results and the second phase achieves little. If the cell is only marginally charged during the first phase, then the second phase acts to remove the charge and thereby bring the cell to a baseline level. If the cell is electroporated then the second phase, by quickly removing the excess charge sitting on the membrane, acts to quickly "heal" the cell.

In the example of the plot 320, the duration of the second phase, at 3.5 ms, is too long and the membrane is actually discharged and taken slightly negative. This is a suboptimal result noting that a second phase duration of about 2.5 ms would have been optimal.

Figure 4:
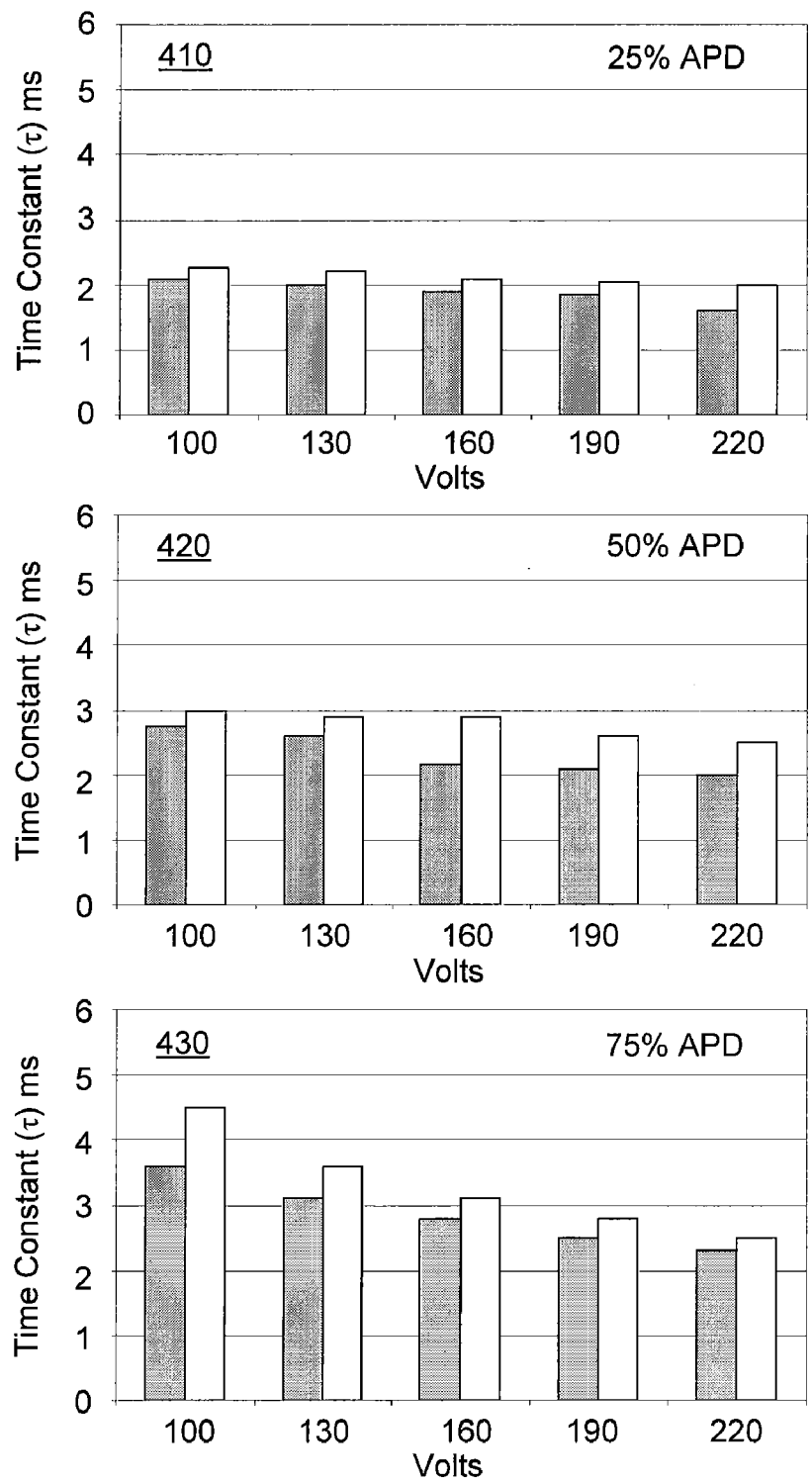
FIG. 4 is a series of plots as taken from a study by Cheng et al. where membrane time constant varies with respect to several factors.

FIG. 4 shows three plots of time constant (t) versus voltage for normal and ischemic conditions in rabbits where shocks were delivered at 25% (plot 410), 50% (plot 420) and 75% (plot 430) of the action potential duration (APD). These data are from a study by Cheng et al., "Mechanisms of shock-induced arrhythmogenesis during acute global ischemia," Am J Physiol Heart Circ Physiol 282: H2141-H2151, 2002. This study induced global acute cardiac ischemia by rapid reduction of the flow rate by 75% where a relatively steady state of action potential duration (APD) was reached between 20 and 30 minutes of the flow reduction. In ischemic and normal conditions, truncated exponential, monophasic shocks of 8 ms in duration were delivered from a 150-pF capacitor defibrillator (HVS-02, Ventritex) between two electrodes (apex and right ventricle). To improve the fidelity of time constant measurement, Cheng et al. used only strong transmembrane responses to the shock (amplitude >10 mV) and traces with a signal-to-noise ratio above 75.

The data in the plots 410, 420 and 430 indicate that, for a truncated exponential, monophasic shock waveform (with positive voltage), time constant of the myocardium decreases with increasing shock voltage, increases with increasing fraction of APD delivery and with ischemia. Result for a negative voltage, i.e., hyperpolarization, differed or were inconclusive for ischemia (particularly at 50% APD) and for fraction of APD (time constant increased with respect to fraction of APD) while trends with respect to voltage were maintained.

Figure 5:
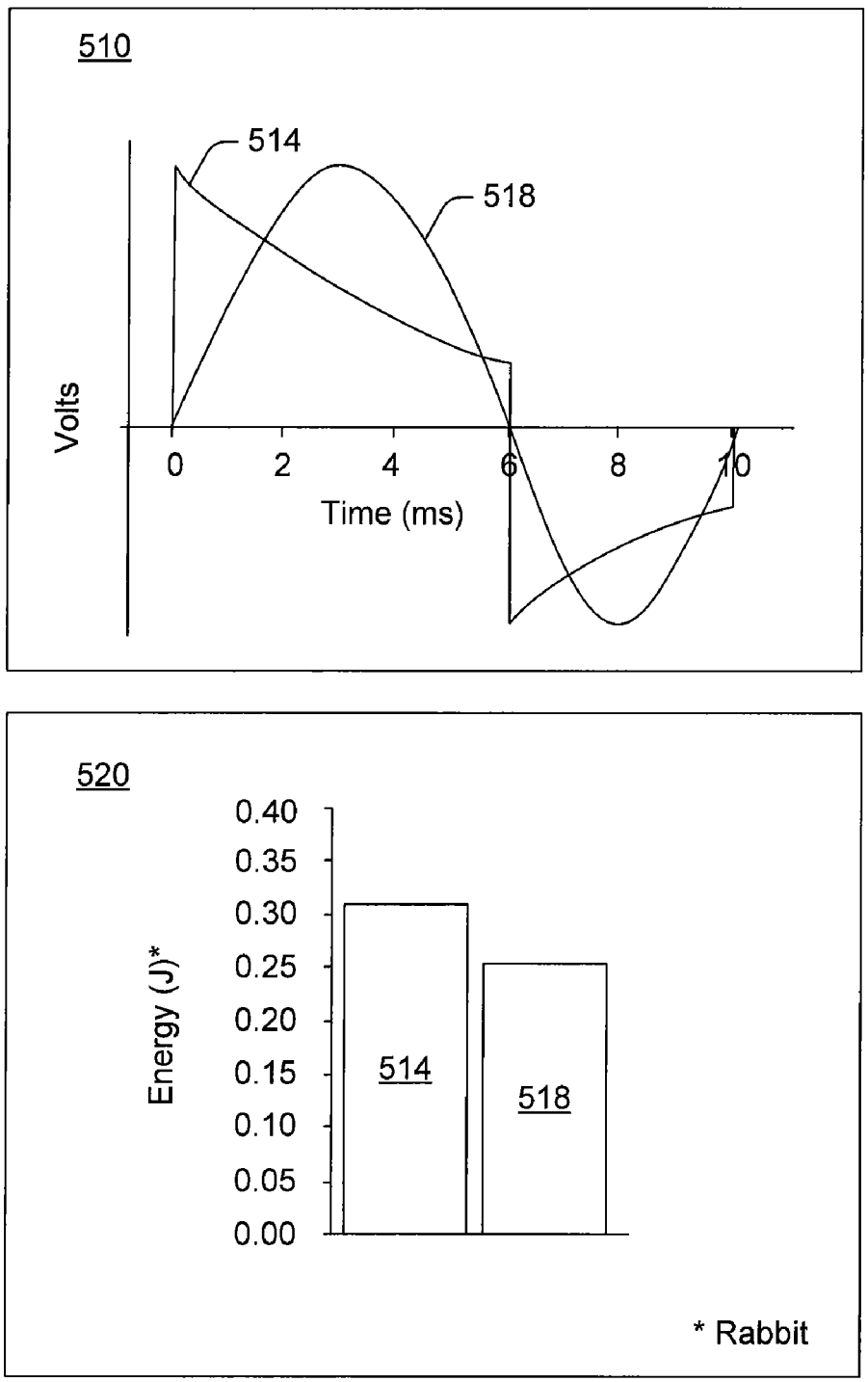
FIG. 5 is a plot of potential versus time for a truncated exponential waveform and a damped sine waveform and a plot of energy required for defibrillation using such waveforms.

FIG. 5 shows a plot 510 of potential versus time for a truncated exponential waveform 514 and a Gurvich waveform 518 and a plot 520 of defibrillation energy for a truncated exponential waveform 514 and a Gurvich waveform 518. A study by Qu et al., "The Gurvich defibrillation waveform has lower defibrillation threshold than the Zoll waveform and the truncated exponential waveform in the rabbit heart," Can. J. Physiol. Phar. 2004 (in press) indicates that the Gurvich waveform (damped sine wave) has a lower threshold than the Zoll or the truncated exponential waveforms. However, another study (Bardy et al., "Truncated Biphasic Pulses for Transthoracic Defibrillation," Circulation. 1995; 91:1768-1774) states that damped sine wave pulses may offer no advantage for ICDs and would result in an increase in ICD size and weight because of the need to generate higher voltages compared to other waveforms. Regardless of this opinion, the type of shock waveform may be an important parameter in determining an optimal shock, recognizing that certain devices may be limited in waveform capabilities.

A study by Mowrey et al., "Kinetics of defibrillation shock-induced response: design implications for the optimal defibrillation waveform," Europace. 2002 January; 4(1):27-39, concluded that the time constant of the membrane depends on the field, action potential phase and the shock polarity and suggested use of a slower shock leading edge, since the membrane cannot follow potentially damaging faster waveforms. Time constants were based on a single exponential model and data for rabbits yielded time constants in a range from 1.6 ms to 14.2 ms.

Figure 6:
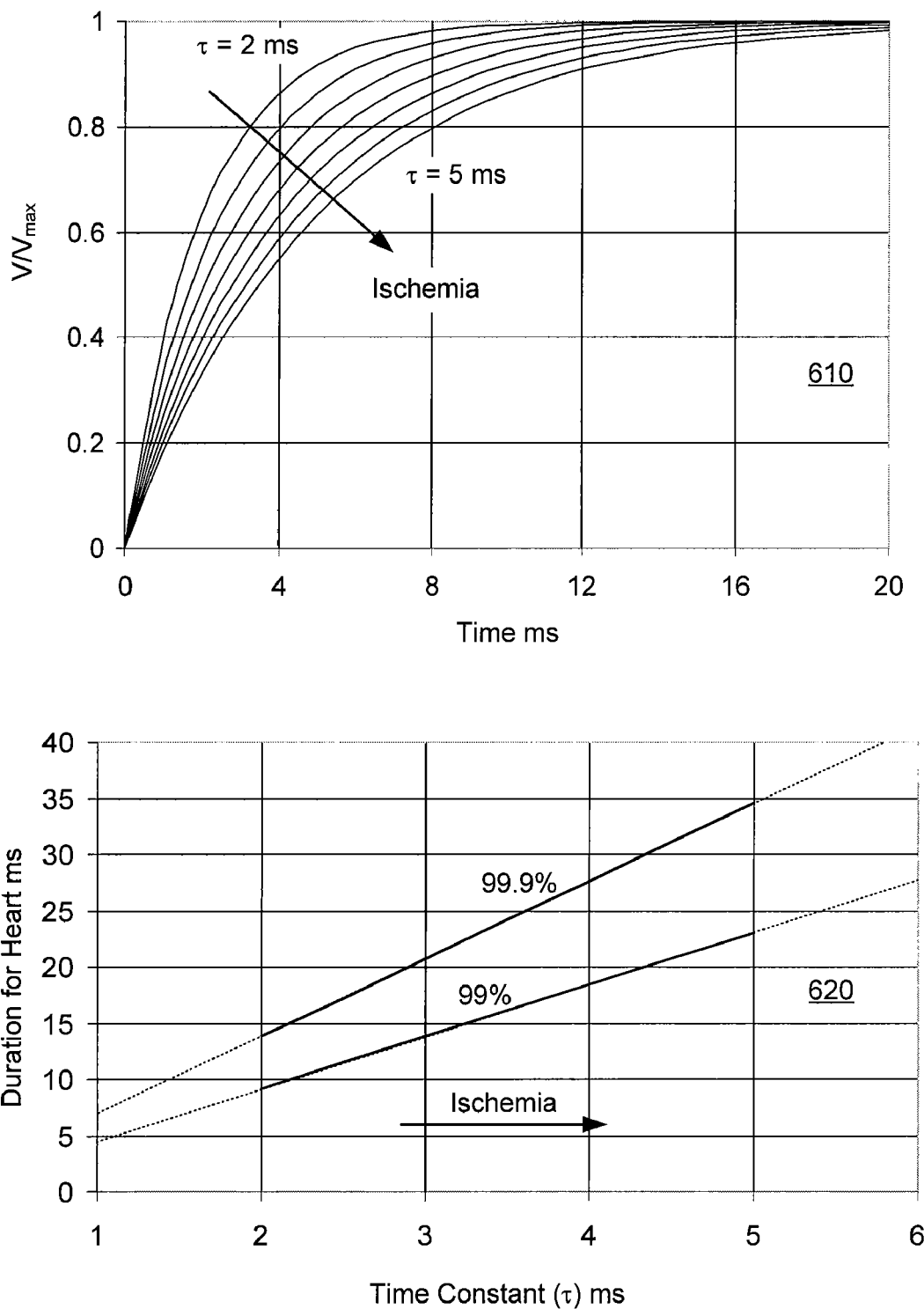
FIG. 6 is a plot of normalized membrane potential versus time for various membrane time constants and a plot of duration to the heart (membrane) to reach a certain normalized membrane potential given a membrane time constant.

FIG. 6 shows a plot 610 of normalized potential versus time and a plot 620 of duration for reaching a particular fraction of maximum potential versus time constant. According to the plot 610, ischemia causes an increase in time constant. According to the plot 620, an increase in time constant due to ischemia corresponds to a longer duration for the myocardium to reach a desired potential (e.g., 99%, 99.9%, etc. of a maximum potential).

Figure 7:
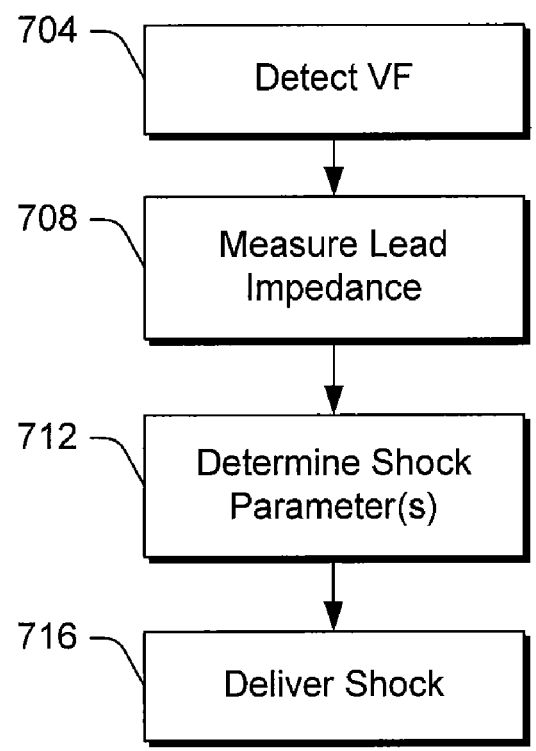
FIG. 7 is a diagram of an exemplary method that aims to defibrillate the heart where measuring occurs at least prior to delivering a shock.

FIG. 7 shows an exemplary method 700 for delivering a defibrillation shock. A detection block 704 detects a need for a shock. While the detection block 704 indicates detection of ventricular fibrillation (VF), other types of arrhythmia may be treated using one or more shocks. A measurement block 708 follows that measures lead impedance. If a recent lead impedance measurement has been made or lead impedance is otherwise known, then the exemplary method 700 may proceed to a subsequent block. The exemplary method 700 follows in a determination block 712 that determines one or more shock parameters based any of a variety of factors. A delivery block 716 delivers the shock according to the one or more parameters. The delivery block 716 may call for delivery of more than one shock as the one or more shock parameters may pertain to more than one shock.

The exemplary method 700 may operate as follows: the detection block 704 may detect ventricular fibrillation; the measurement block 708 may measure impedance of a defibrillation circuit that includes myocardial tissue; the determination block 712 may determine one or more defibrillation shock parameters based at least in part on the impedance; and the delivery block 716 may deliver a defibrillation shock using the one or more defibrillation shock parameters. Further, if the shock was unsuccessful, the exemplary method may adjust a membrane time constant and then determine one or more new defibrillation shock parameters based at least in part on the adjusted membrane time constant. Such an exemplary method may relate an increase in the membrane time constant to presence of ischemia or worsening of ischemia. In the case the shock was successful, one or more parameters may be stored or analyzed to yield a membrane time constant.

Figure 8:
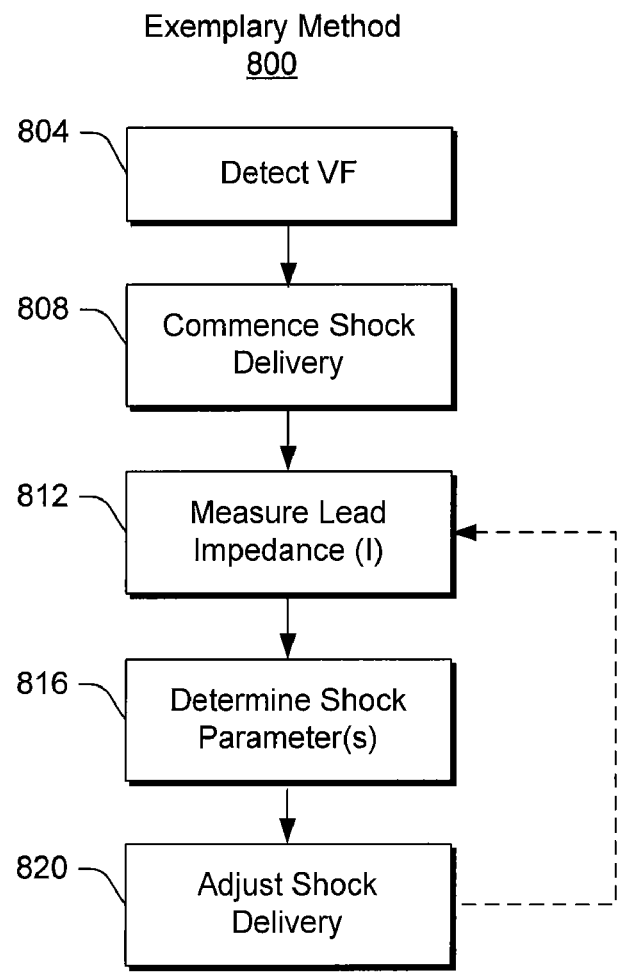
FIG. 8 is a diagram of an exemplary method that aims to defibrillate the heart where measuring occurs during a delivering period of a shock.
Figure 8:
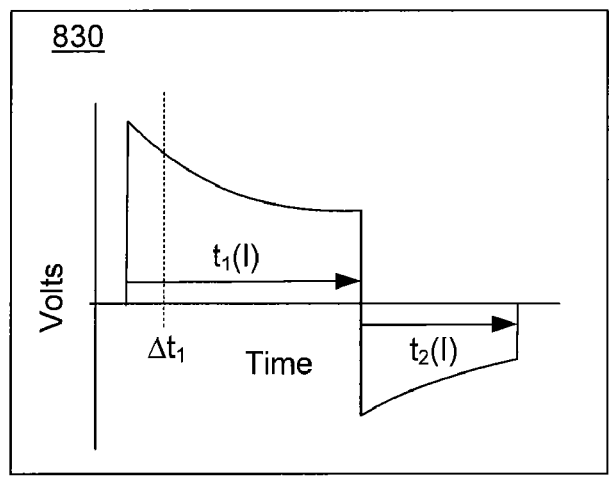

FIG. 8 shows an exemplary method 800 for delivering a defibrillation shock that includes measuring during delivery of the shock and an exemplary plot 830 of voltage versus time where a parameter (e.g., duration) depends at least in part on the measuring. A detection block 804 detects a need for a shock. While the detection block 804 indicates detection of ventricular fibrillation (VF), other types of arrhythmia may be treated using one or more shocks. A commencement block 808 follows that commences delivery of a defibrillation shock. A measurement block 812 follows that measures lead impedance. For example, for a biphasic shock, the first phase generally exceeds 3 ms. Thus, in this example, about 1 ms after commencement of the shock, measurement of voltage and current may occur. Impedance may then be approximated by the voltage divided by the current.

A determination block 816 may rely on this impedance (or other measurement, etc.) may be used to adjust one or more shock parameters such as shock duration. An adjustment block 820 adjusts one or more shock parameters, if required. An adjustment can include terminating the shock. For a biphasic shock, consider the plot 830, where an on-the-fly measurement (e.g., at $\Delta t_1$) or measurements may be used to determine or adjust shock duration of the first phase ($t_1$), the second phase ($t_2$) or an overall duration (e.g., $t_1+t_2$). Of course, other parameters may be adjusted in addition to or alternative to shock duration. Further measurements, determinations and adjustments may occur, as represented by the dashed line that loops from the adjustment block 820 to the measurement block 812. Various exemplary methods optionally include measuring prior to commencement of a shock and during commencement of a shock.

Various exemplary methods may make determinations or adjustments using additional information, which may be information measured in vivo, information acquired via wireless communication, etc.

As mentioned for the exemplary method 700, if the shock was unsuccessful, the exemplary method 800 may adjust a membrane time constant and then determine one or more new defibrillation shock parameters based at least in part on the adjusted membrane time constant. Such an exemplary method may relate an increase in the membrane time constant to presence of ischemia or worsening of ischemia. In the case the shock was successful, one or more parameters may be stored or analyzed to yield a membrane time constant.

Various exemplary methods optionally rely on selection of a membrane time constant and determining one or more shock parameters based on the selected constant, which may be implemented in a determination block such as the block 712 or the block 816. If a shock is unsuccessful, rather than adjusting the one or more shock specific parameters (e.g., duration, voltage, tilt, etc.), the membrane time constant is adjusted upward or downward. In response, one or more new shock parameters are determined based on the adjusted membrane time constant. In such exemplary methods, the membrane time constant becomes an important factor in defibrillation therapy. Further, actual measurement of the membrane time constant may not be required. Instead, a model relates one or more shock parameters to a membrane time constant. In other exemplary methods, the membrane time constant may be used to determine only a single shock parameter, for example, shock duration. In yet other exemplary methods, leading edge voltage and membrane time constant may be used to determine shock duration. Of course, membrane time constant can be used in a variety of manners in determining one or more shock parameters.

Various exemplary methods optionally rely on changes to one or more shock parameters to estimate a membrane time constant. This approach may be referred to as an inverse approach. In such exemplary methods, information stored by an ICD may be analyzed to determine a membrane time constant or a change in membrane time constant over time. The values may then be related to ischemia (see, e.g., the plots of FIG. 4).

An exemplary method that aims to defibrillate the heart may use defibrillation waveforms based on cardiac membrane response to one or more shocks where adjustments may occur to an assumed membrane time constant in response to an unsuccessful shock. An exemplary method that aims to defibrillate the heart may detect ischemia and in response to the detection, adjust duration of a defibrillation shock, typically to lengthen the duration.

Various exemplary methods optionally rely on ischemia detection by any of a variety of techniques (e.g., sensors, parameter changes, etc.) and then use such information to select an appropriate membrane time constant for use in determining one or more shock parameters. For example, as shown in the plots of FIG. 4, if ischemia is present, then membrane time constant has increased and may increase further if the ischemia progresses.

Figure 9:
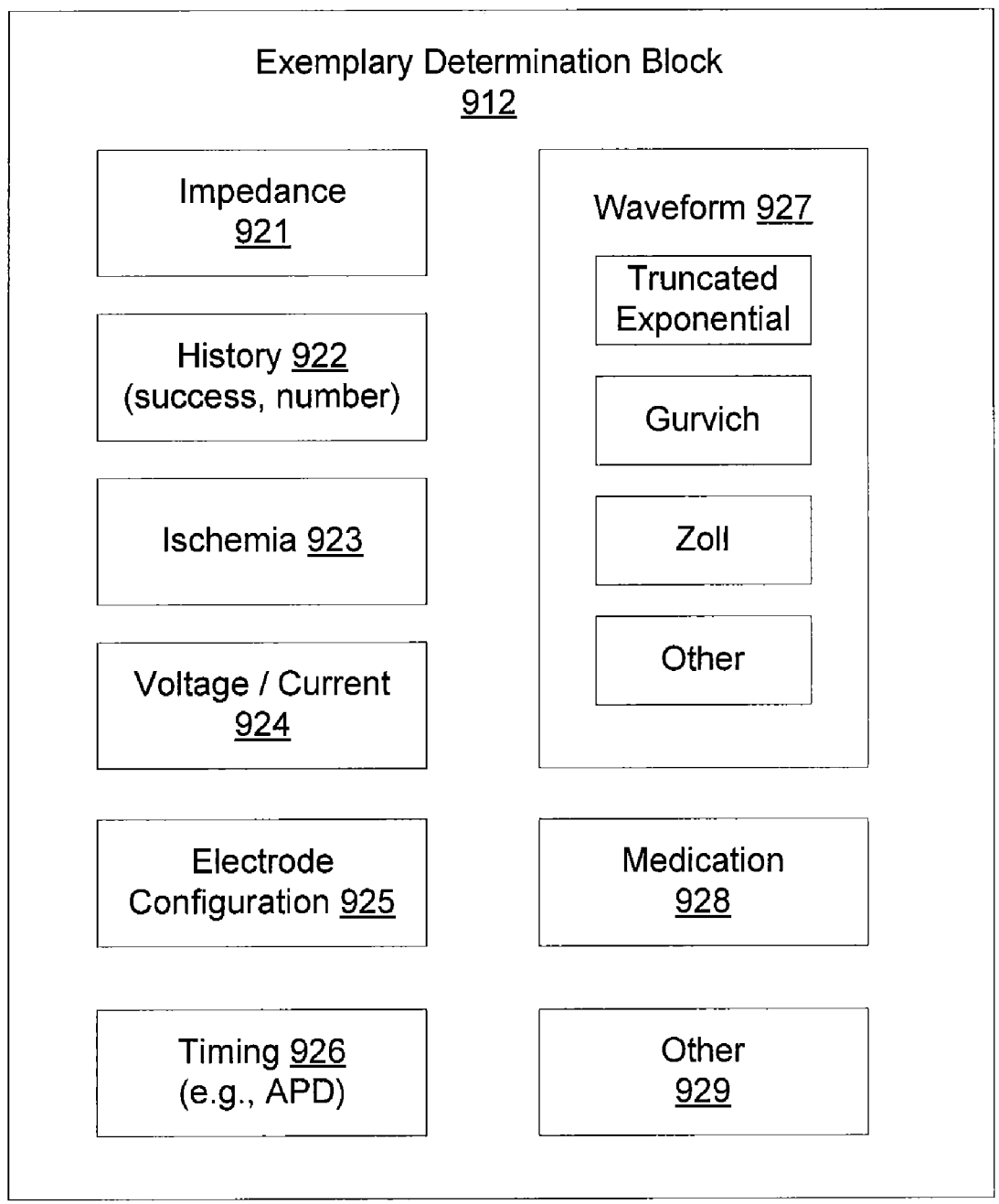
FIG. 9 is a diagram of an exemplary determination block that may determine one or more defibrillation shock parameters.

FIG. 9 shows an exemplary determination block 912, which may serve as the determination block 712 of the exemplary method 700 or the determination block 816 of the exemplary method 800. The determination block 912 includes various sub-blocks 921-929. More specifically, the listed sub-blocks include sub-blocks for impedance 921, history 922, ischemia 923, voltage/current 924, electrode configuration 925, timing 926, waveform 927, medication 928 and other 929. An exemplary determination block may rely on one or more of such sub-blocks. The sub-blocks 921-929 may represent inputs or outputs. Inputs are generally various factors that may be used to determine one or more output parameters. Various features of the exemplary determination block 912 may be included in an exemplary implantable device, such as, but not limited to, the exemplary device 100 of FIGS. 1 and 2 (see, e.g., the module 239, etc.).

With respect to impedance 921, a study by Inrich "How to program pulse duration or tilt in implantable cardioverter defibrillators," Pacing Clin Electrophysiol. 2003 January; 26(1 Pt 2):453-6, presented a system of three related equations: a tilt equation, a pulse duration equation and an RC time constant equation, where "R" is the output resistance or impedance and "C" is the output capacitance. Inrich based the RC time constant on knowledge of the pulse generator's output capacitance and the lead system's resistance. With this value and an assumed chronaxie time (the pulse duration at which twice the rheobase current is required to evoke a threshold response), Inrich presented a manner to obtain "the optimal values to which the PD and tilt should be programmed." Inrich further suggested a "realistic range" for the RC time constant from about 2.5 ms to about 9 ms and a relationship where tilt decreases over this range from about 65% to about 45%.

With respect to chronaxie time constant and membrane time constant, a study by Swerdlow et al. "Application of Models of Defibrillation to Human Defibrillation Data: Implications for Optimizing Implantable Defibrillator Capacitance," Circulation, 1997; 96: 2813-2822, presented model time constants and predicted optimal biphasic waveforms for epicardial and transvenous deliveries. Such information may be used in determining one or more shock parameters.

The history sub-block 922 may introduce information pertaining to past success or number of prior shocks when determining a shock parameter. The ischemia sub-block 923 may introduce ischemia information that is optionally related to trends reported in the aforementioned study by Cheng et al. The voltage/current sub-block 924 may introduce information as to voltage, current, energy, etc., of past shocks or limitations of an implantable device. The electrode configuration sub-block 925 may introduce information pertaining to location or type of an electrode or electrodes. As already mentioned, epicardial and transvenous shocks may use different shock parameters. The timing sub-block 926 may introduce information pertaining to the timing of a shock with respect to, for example, an action potential. The waveform sub-block 927 may introduce information related to type of waveform and phase. The medication sub-block 928 may introduce information as to medication taken by a patient that could have an effect on shock therapy or risk of fibrillation or other arrhythmia. The "other" sub-block 929 is included as to cover various other factors that may be used to optimize one or more shock parameters.

The exemplary determination block 912 may rely on one or more inputs to determine or estimate a myocardial time constant. Once such a time constant has been determined, then a look-up table, a model, etc., may be used to select one or more shock parameters, preferably parameters deemed optimal for termination of ventricular fibrillation. Such a determination may occur during delivery or prior to delivery of a shock. In either instance, upon delivery of a shock based on such parameters, success or failure may be noted (e.g., stored) or used in a feedback loop to optimize defibrillation success. Such information may be useful in diagnosing patient condition or future therapy.

The exemplary determination block 912 may include control logic for controlling actions of an exemplary implantable device. Such logic is optionally implemented as instructions on one or more computer readable media that can, for example, enable a microprocessor to operate accordingly. Referring again to the exemplary device 100 of FIGS. 1 and 2, such a device may include logic for determinations or other actions. For example, an exemplary device may optionally include control logic to detect fibrillation, to determine one or more defibrillation shock parameters based at least in part on a measured impedance, to call for delivery a defibrillation shock using a lead and the one or more defibrillation shock parameters, to decide whether the shock was unsuccessful and, if the shock was unsuccessful, to adjust a membrane time constant and to determine one or more new defibrillation shock parameters based at least in part on the adjusted membrane time constant.

In another example, an exemplary device may optionally include control logic to detect fibrillation, to decide whether a patient has cardiac ischemia, to select a defibrillation shock duration based at least in part on the deciding, to deliver a defibrillation shock using a lead and the selected defibrillation shock duration, to decide whether the shock was unsuccessful and, if the shock was unsuccessful, to adjust the defibrillation shock duration and to deliver another defibrillation shock using the adjusted defibrillation shock duration.

In yet another example, an exemplary device may optionally include control logic to determine cardiac membrane time constants based at least in part on stored defibrillation shock parameters and to decide whether a patient has ischemia. In another example, an exemplary device may optionally include control logic to detect fibrillation, to commence delivery of a defibrillation shock using a lead, to determine one or more defibrillation shock parameters based at least in part on a measured impedance and to adjust one or more defibrillation shock parameters during delivery of a defibrillation shock. Of course, other examples exist, which may rely on control logic to implement various exemplary methods, such as, but not limited to, the exemplary methods 700, 800, 1000, 1100, and 1200.

Figure 10:
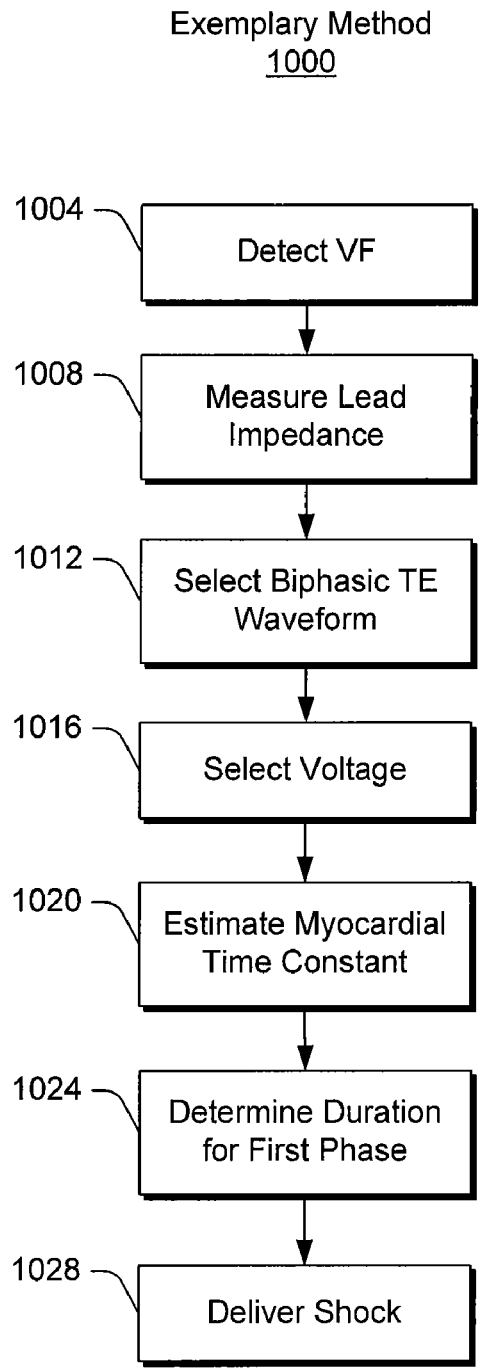
FIG. 10 is a block diagram of an exemplary method that aims to defibrillate the heart based at least in part on an estimated membrane time constant.

FIG. 10 shows an exemplary method 1000 for delivering a defibrillation shock. In a detection block 1004, detection of ventricular fibrillation occurs. A measurement block 1008 follows that measures lead impedance. A selection block 1012 selects a particular waveform or uses a default waveform, for example, a biphasic truncated exponential (TE) waveform. Based on the impedance and selected waveform, another selection block 1016 selects a voltage, for example, a leading edge voltage of a defibrillation shock. The exemplary method 1000 then estimates a myocardial time constant (e.g., a membrane time constant, $\tau$) in an estimation block 1020, for example, based on historic information. Given the waveform type, the leading edge voltage and the estimated time constant, a determination block 1024 determines duration for a first phase of the biphasic waveform. In general, the duration aims to avoid waste of energy, i.e., to achieve capture without delivering excessive charge to the myocardial tissue. A delivery block 1028 follows where a shock is delivered in an effort to defibrillate the heart.

Various exemplary methods optionally include a measurement block that measures impedance after commencement of a shock. Based on the impedance and selected waveform, a block may select a voltage, for example, based optionally in part on duration since commencement of the shock. Such an exemplary method may estimate a myocardial time constant (e.g., a membrane time constant, $\tau$), for example, as in the exemplary method 1000. On the basis of the measured information or other information, a determination block may determine a duration for a first phase of the biphasic waveform and an adjustment block may adjust the duration of the first phase during delivery of the shock. Of course, such an exemplary method may operate during a subsequent phase or during delivery of other types of waveforms.

Figure 11:
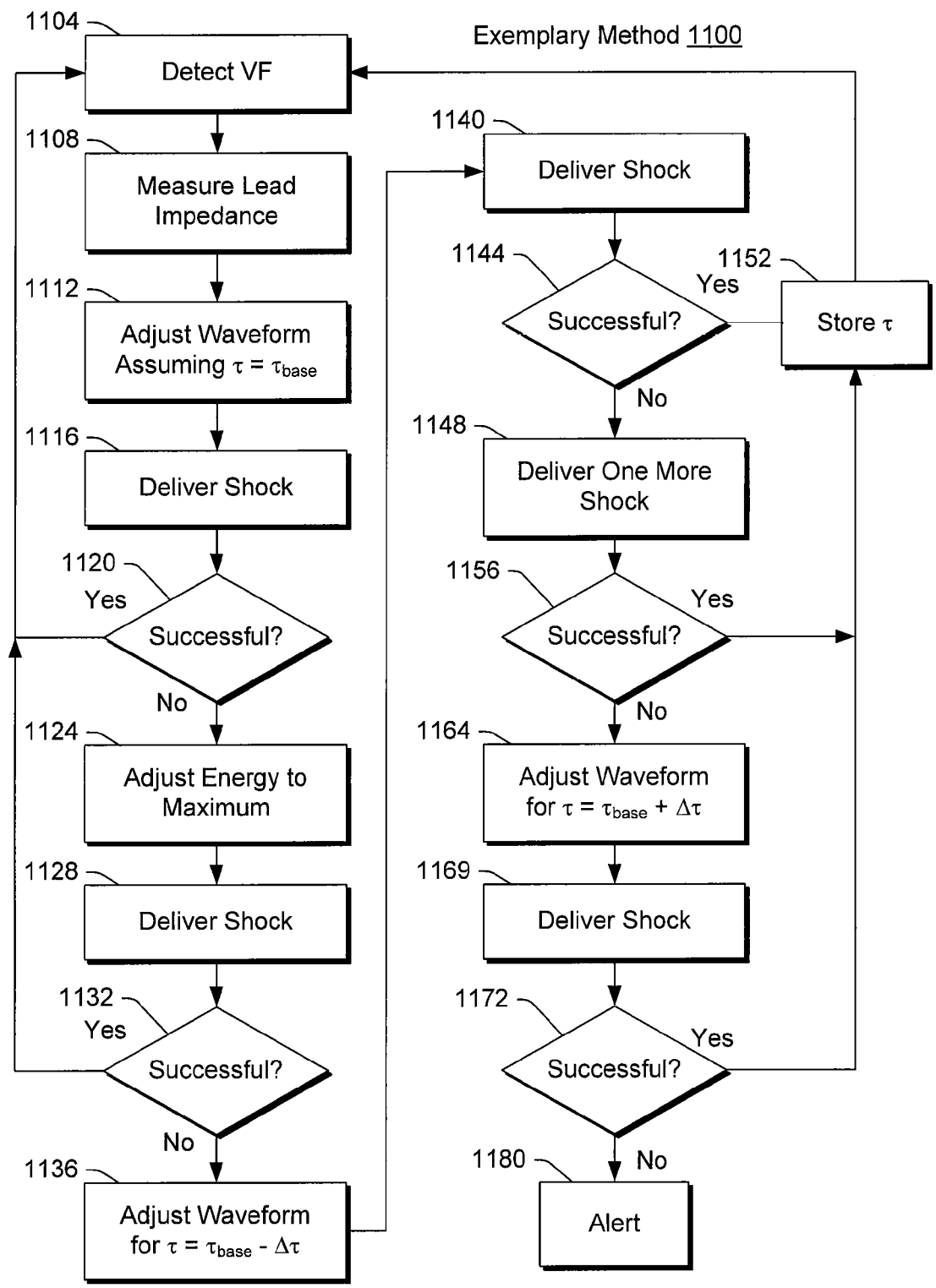
FIG. 11 is a block diagram of an exemplary method that aims to defibrillate the heart and store information pertaining to membrane time constant.

FIG. 11 shows an exemplary method 1100 for defibrillation of the heart. The exemplary method 1100 commences in a detection block 1104 that detects ventricular fibrillation. A measurement block 1108 then measures impedance between two or more electrodes intended for delivery of a defibrillation shock to the heart. Based at least in part on the measured impedance, the method 1100 adjusts a defibrillation shock waveform assuming a membrane time constant $\tau=\tau_{base}$, for example, of approximately 3.5 ms. The adjustment may act to adjust the duration of the waveform to minimize delivery of excessive energy to the myocardium. A delivery block 1116 follows that delivers a defibrillation shock using the adjusted waveform.

The exemplary method 1100 then continues with a decision block 1120 that decides whether the defibrillation shock was successful. If the delivered shock was a success, then the method 1100 may continue at the detection block 1104 where normal monitoring may occur. However, if the delivered shock did not successfully defibrillate the heart, then the method 1100 continues in another adjustment block 1124 that adjusts the shock energy upward, for example, to a maximum. In general, a defibrillation method should aim to defibrillate the heart in an expedient manner. Thus, if an initial shock does not succeed, then the next shock should typically have a greater probability of success, even though shock energy may be in excess of the optimal shock energy. A delivery block 1128 delivers the shock at the higher energy, while still relying on the membrane time constant $\tau_{base}$.

Another decision block 1132 follows delivery of the higher energy shock. If the higher energy shock successfully defibrillated the heart, then the method 1100 continues at the detection block 1104. However, if the higher energy shock does not succeed in defibrillating the heart, then the method 1100 continues in a waveform adjustment block 1136 that relies on a different membrane time constant, for example, according to the equation: $\tau=\tau_{base}-\Delta\tau$. A shock delivery block 1140 follows the adjustment block 1136.

Thus, to this point, the exemplary method 1100 has delivered two shocks using a waveform based at least in part on a base membrane time constant and a third shock using a waveform based at least in part on an adjusted membrane time constant. In general, the third shock is delivered using a high energy level, for example, a maximum energy. After delivery of the third shock per the delivery block 1140, the method 1100 enters yet another decision block 1144 that decides if the shock successfully defibrillated the heart. If the shock was successful, then the method 1100 stores the associated membrane time constant (e.g., the constant of the block 1136) in a storage block 1152 and may return to the detection block 1104. However, if the third shock does not succeed, then another delivery block 1148 may follow and deliver one more shock. Similarly, another decision block 1156 may follow the delivery block 1148. In the instance that the additional shock does not succeed in defibrillating the heart, then another adjustment may occur in an adjustment block 1164 where the membrane time constant is adjusted according to the equation: $\tau=\tau_{base}+\Delta\tau$.

A delivery block 1169 delivers a shock according to the adjusted membrane constant and a decision block 1172 decides to store the membrane time constant via the storage block 1152 if the shock successfully defibrillates the heart or it may issue an alert per the alert block 1180 if the shock does not succeed.

While the exemplary method 1100 includes a measurement block 1108 prior to the delivery block 1116, a measurement block may be implemented during delivery of a shock, between phase switching or at other times during the overall shock duration. Such measured information may be used to determine or adjust one or more shock parameters during delivery or prior to delivery of a subsequent shock (e.g., delivery block 1128, 1140, 1169). A measurement block may be implemented during delivery, between phase switching or at other times during the overall shock duration of shocks associated with one or more of the delivery blocks 1128, 1140 and 1169.

Various exemplary methods optionally rely on an initial membrane time constant and one or more adjustments to such a value to determine one or more defibrillation shock parameters. For shocks that succeed in defibrillation, the membrane time constant may be stored or normalized and stored.

Figure 12:
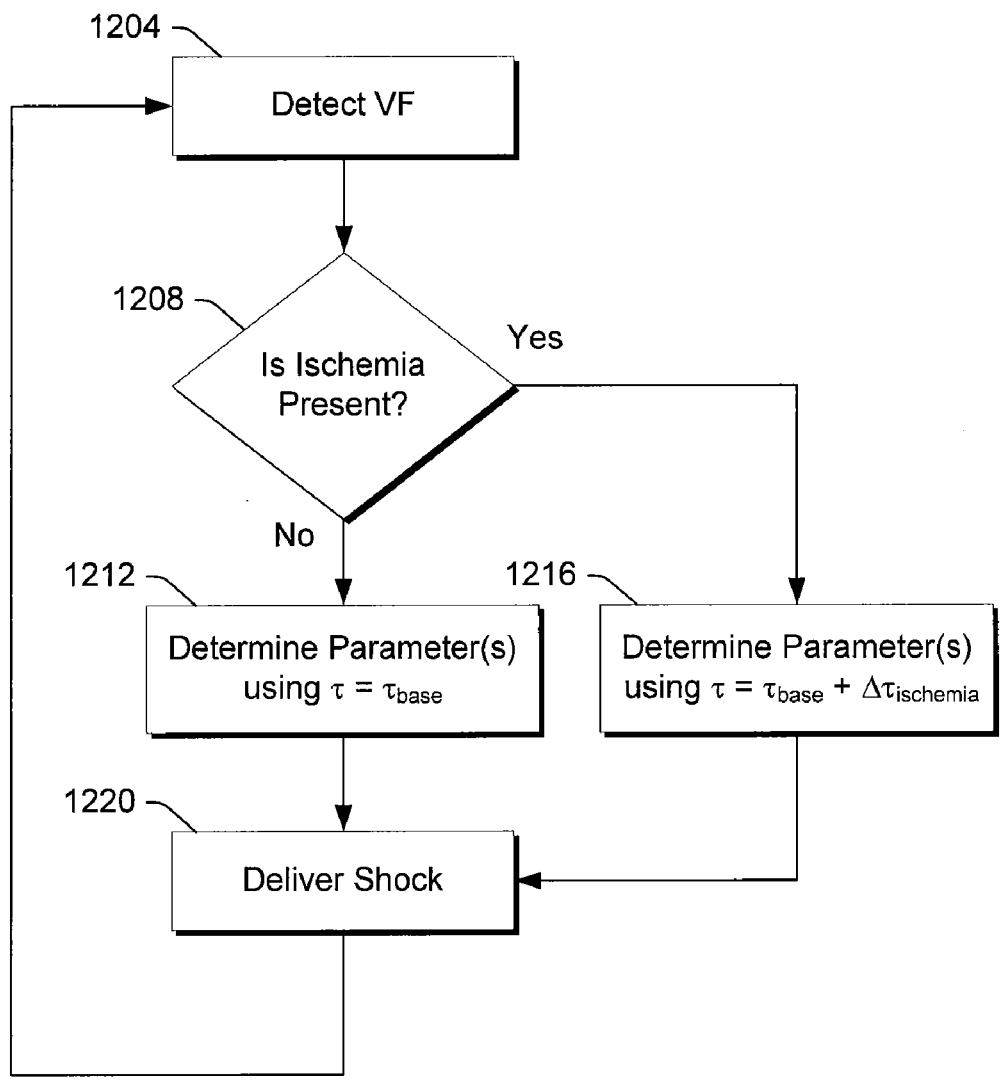
FIG. 12 is a block diagram of an exemplary method that decides if ischemia is present and then selects a membrane time constant based on the decision, which may aid in determining one or more defibrillation shock parameters.

FIG. 12 shows an exemplary method 1200 for delivering a defibrillation shock. According to the exemplary method 1200, a detection block 1204 detects ventricular fibrillation. A decision block 1208 follows that decides if ischemia is present. Information for making such a decision may come from any of a variety of sensors or from an external source via wireless communication (e.g., transtelephonic communication, etc.). If the decision block 1208 decides that ischemia is not present, then a determination block 1212 determines one or more shock parameters using a base membrane time constant ($\tau = \tau_{base}$). However, if the decision block 1208 decides that ischemia is present, then a determination block 1216 determines one or more shock parameters using a membrane time constant that is greater than the base time constant (e.g., $\tau = \tau_{base} + \Delta\tau_{ischemia}$). The membrane time constant in the case of ischemia is optionally selected based on degree of ischemia. For example, a $\Delta\tau_{ischemia}$ may vary depending on degree of ischemia.

Figure 13:
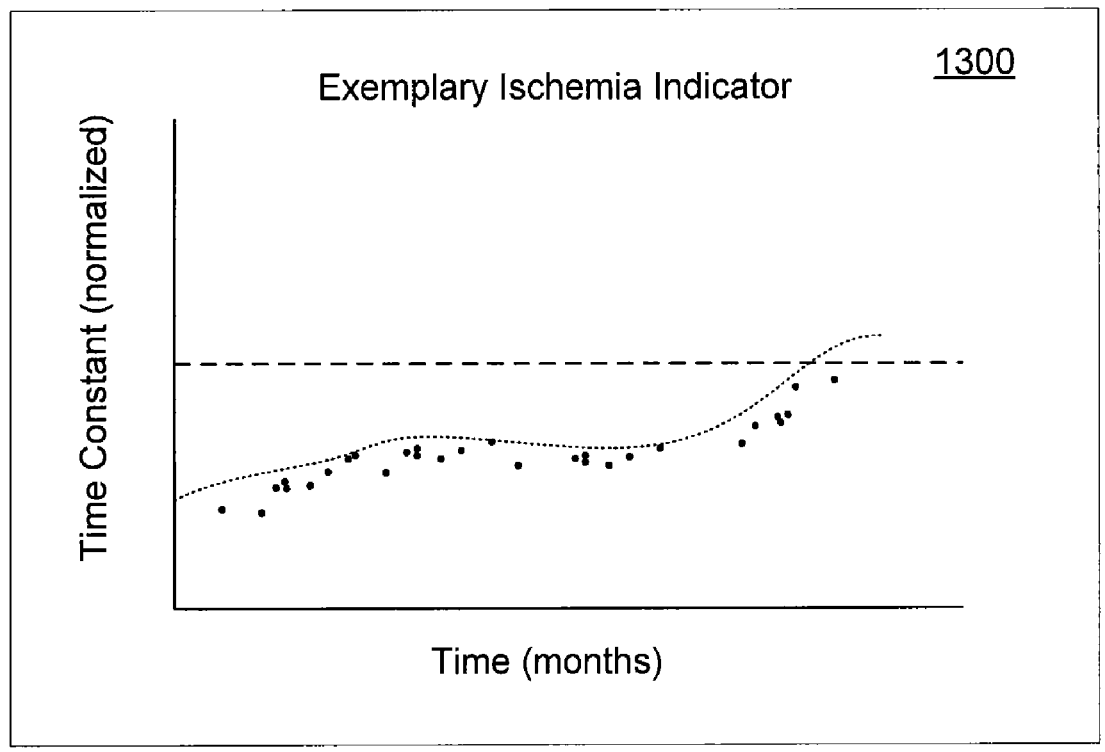
FIG. 13 is a plot of an exemplary ischemia indicator plotted as normalized membrane time constant versus time in months.

FIG. 13 shows an exemplary ischemia indicator plot 1300 of membrane time constant, optionally normalized, versus time in months. The solid line represents successful shocks while the individual points represent unsuccessful shocks. A dashed line represents an optional alert level based on membrane time constant exceeding a certain value. Shock frequency for ICD patients can vary from less than once per month to more than once per day. Defibrillation thresholds have been reported to vary with circadian, seasonal and other rhythms. Such variations may be expected with respect to membrane time constant as well. However, as shown in FIG. 4, ischemia corresponds to an increase in membrane time constant. Further, ischemia may occur over a time-scale that exceeds such other rhythms. Consequently, varying shock parameters on the basis of membrane time constant can provide useful information as to ischemia.

Various exemplary methods optionally deliver atrial shocks which may similarly rely on a membrane time constant. Further, atrial shocks may be delivered more frequently than ventricular shocks, which, in turn, may allow for a better indication of ischemia.

Although exemplary methods, devices, systems, etc., have been described at times in language specific to structural features or methodological acts, it is to be understood that the subject matter defined in the appended claims is not necessarily limited to the specific features or acts described. Rather, the specific features and acts are disclosed as exemplary forms of implementing various claimed subject matter.

What is claimed is:

1. A method comprising:
   detecting fibrillation;
   measuring impedance of a defibrillation circuit that includes myocardial tissue;
   determining one or more defibrillation shock parameters based at least in part on the impedance assuming a baseline membrane time constant;
   delivering a defibrillation shock using the one or more defibrillation shock parameters;
   if the shock was unsuccessful, determining one or more new defibrillation shock parameters based at least in part on an adjusted membrane time constant, wherein the adjusted membrane time constant is different from the baseline membrane time constant; and
   delivering a subsequent defibrillation shock using the one or more new defibrillation shock parameters.

2. The method of claim 1 further comprising storing membrane time constants associated with successful defibrillation shocks.

3. The method of claim 1 wherein the determining relies in part on an RC circuit model.

4. The method of claim 1 wherein the defibrillation shock has a biphasic, truncated exponential waveform.

5. The method of claim 1 wherein the one or more defibrillation shock parameters include at least one of leading edge voltage, tilt and shock duration.

6. The method of claim 5 wherein the shock duration parameter corresponds to duration of a first phase of a biphasic waveform.

7. The method of claim 1 wherein the defibrillation shock has a positive voltage.

8. The method claim 1 wherein the adjusted time membrane constant is less than the baseline time membrane constant.

9. The method of claim 1 further comprising:
   if the subsequent shock was unsuccessful, determining one or more other new defibrillation shock parameters based at least in part on another adjusted membrane time constant, wherein the other adjusted membrane time constant is different from both the baseline membrane time constant and the adjusted membrane time constant; and
   delivering another subsequent defibrillation shock using the one or more other new defibrillation shock parameters.

10. The method of claim 9 wherein the other adjusted time membrane constant is greater than the baseline time membrane constant.

11. A method comprising:
    detecting fibrillation;
    measuring impedance of a defibrillation circuit that includes myocardial tissue;
    determining one or more defibrillation shock parameters based at least in part on the impedance;
    delivering a defibrillation shock using the one or more defibrillation shock parameters;
    if the shock was unsuccessful, adjusting a membrane time constant and determining one or more new defibrillation shock parameters based at least in part on the adjusted membrane time constant; and
    relating an increase in the membrane time constant to presence of ischemia or worsening of ischemia.

12. A method comprising:
    providing a history of one or more defibrillation shock parameters for a patient fitted with an ICD;

determining a corresponding history of membrane time constants based at least in part on the history of defibrillation shock parameters; and deciding whether the patient has ischemia based on changes in membrane time constants over time.

13. The method of claim 12 wherein the history spans more than one month.

14. The method of claim 12 wherein the determining relies on a model.

15. The method of claim 12 wherein the one or more defibrillation shock parameters includes defibrillation shock duration.

16. An implantable apparatus comprising:

memory operative to store one or more defibrillation shock parameters; and control logic to determine a corresponding history of cardiac membrane time constants based at least in part on stored defibrillation shock parameters and to decide whether the patient has ischemia based on changes in membrane time constants over time.

* * * * *